United States Patent [19]
Schneider, Sr.

[11] Patent Number: 5,833,711
[45] Date of Patent: Nov. 10, 1998

[54] METHOD AND MEANS FOR PORTABLE EMERGENCY CARDIOPULMONARY RESUSCITATION

[75] Inventor: Charles W. Schneider, Sr., Kalamazoo, Mich.

[73] Assignee: Cardi-Act, L.L.C., Kalamazoo, Mich.

[21] Appl. No.: 630,408

[22] Filed: Apr. 1, 1996

[51] Int. Cl.⁶ ................................................. A61H 31/00
[52] U.S. Cl. ................................................. 607/3; 601/151
[58] Field of Search ........................ 607/3, 149; 601/150, 601/151

[56] References Cited

U.S. PATENT DOCUMENTS

| | | |
|---|---|---|
| 2,869,537 | 1/1959 | Chu . |
| 3,511,275 | 5/1970 | Hewson . |
| 3,896,797 | 7/1975 | Bucur . |
| 3,961,626 | 6/1976 | Houchen et al. . |
| 4,060,079 | 11/1977 | Reinhold, Jr. . |
| 4,077,400 | 3/1978 | Harrigan . |
| 4,349,015 | 9/1982 | Alferness . |
| 4,362,153 | 12/1982 | Wilson et al. . |
| 4,397,306 | 8/1983 | Weisfedlt et al. . |
| 4,424,806 | 1/1984 | Newman et al. . |
| 4,523,579 | 6/1985 | Barry . |
| 4,664,098 | 5/1987 | Woodenberg et al. . |
| 4,928,674 | 5/1990 | Halperin et al. . |
| 5,078,134 | 1/1992 | Heilman et al. . |
| 5,222,478 | 6/1993 | Scarberry et al. . |
| 5,353,793 | 10/1994 | Bornn ..................................... 128/696 |

*Primary Examiner*—Scott M. Getzow
*Attorney, Agent, or Firm*—Waters & Morse, P.C.

[57] ABSTRACT

A portable device and method for the application of emergency CPR in remote or field locations comprises the use of a vest-like thoracic garment with straps for quickly fastening it about the chest area of a heart-attack victim. The vest contains bladders to provide pneumatic pressure to effect cardiopulmonary resuscitation, and has integrated-circuit controls for inflation; various functions are set at an initail-rate which can be changed during operation. Inflation of the bladders is provided by bottled air or oxygen, or a gas generator. In one embodiment, a mechanical method of flexing the bladders eliminates dependence on stored air. Means for controlling and monitoring the cardiac and/or pulmonary functions of a victim include built-in defibrillation contacts and gauges to observe cardiac and lung functions. Breathing-assistance apparatus is preferably included. Power to operate the device can he supplemented until transfer of the victim to a primary-care facility.

9 Claims, 3 Drawing Sheets

METHOD AND MEANS FOR PORTABLE EMERGENCY CARDIOPULMONARY RESUSCITATION

BACKGROUND OF THE INVENTION

1. Field of the invention

This invention is in the field of medical apparatus, and the method of its use. More specifically, the present invention is in the field of portable apparatus and the method for providing emergency field cardiopulmonary resuscitation (CPR) support for a person whose vital functions may require such emergency assistance.

2. Description of the Prior Art

CPR provides external cardiac stimulation and respiratory support for a person whose heart has ceased functioning for any of a number of reasons, including, inter alia, cardiac arrest, electric shock and drowning. Contemporaneous artificial respiration is necessary to maintain oxygen flow as well.

Although one person can apply CPR for a limited time in an emergency, the acceptable manual application of CPR involves a minimum of two people due at least in part to the physical exertion involved in the application of manual CPR, it is desirable to have at least one additional person available to serve as a relief. However, especially where field operations are concerned, the availability of persons trained in CPR is likely to he quite limited. For this reason, mechanical systems to apply CPR have been developed, including those described in U.S. Pat. No. 4,424,806 to Newman et al. (Newman). The Newman apparatus comprises a vest circumscribing the torso of a victim, the vest containing a first inflatable bladder overlying the victim's chest and a second inflatable bladder overlying the abdominal region.

Portable or easily-stored CPR apparatus is of particular utility for use in field applications, such as rescue-team and ambulance work, life-guard stations and the like, and such apparatus is known in the art, such as described by Bucur, in U.S. Pat. No. 3,986,797. However, the Bucur apparatus employs a plunger to provide what is substantially a single-point compression on the sternum for cardiac stimulation, and requires a fixed mounting for its use.

Another apparatus of the prior art is that of Halperin et al., described in U.S. Pat. No. 4,928,674 (Halperin). As with Newman, the Halperin device provides a vest to circumscribe the thoracic region of a victim, the vest containing a biasing bladder for urging an inflatable bladder against the chest wall of the victim, the inflatable bladder being a means to provide variable intrathoracic pressure.

Chu, in U.S. Pat. No. 2,869,537, describes a device for providing assistance to one suffering from emphysema or other thoracic problem, comprising a flexible vest having inflatable air bags for providing fluctuating intrathoracic pressure, and particularly for providing external pressure to the thoracic region to assist in expelling inspired air from the lungs of the person suffering from emphysema.

Some prior-art devices have filled a need for field CPR apparatus, but nevertheless continue to require the full attention of at least one, and often, more, rescue or emergency personnel; most devices, however, require essentially full hospital facilities and trained personnel for their operation. Even with portable apparatus, problems such as getting the victim into or onto the CPR device, and monitoring vital signs or adjusting the heart or respiratory functions of the apparatus occupy treating personnel after the machine has been put into operation. Other than the vest of Chu, prior-art devices generally require an external control for the rate and magnitude of fluctuation of the pressure of the inflatable air bags.

A further problem occurring with any device which must be stored indefinitely against future need is that of power. Such a device must either carry a storage means such as a battery, or depend on exterior power sources such as residential line voltage or an automotive battery. In the particular case of a CPR device, the apparatus could be stored in an emergency vehicle for an extended period of time before being used, with standby charging means maintaining a full battery charge. However, the amount of energy necessary for powering the cardiac-stimulation means is such that a battery could be quickly depleted, unless its size is large enough to sustain protracted use; in the latter circumstance, the size and weight of the battery can impede the ready use of the CPR device.

An inspection of the devices of the prior art shows that they are generally intended for institutional or clinical use, requiring either the attention of at least semi-skilled personnel, or external power or control means, or any combination of these factors. However, none of the prior-art devices appears to be useful by unskilled personnel or capable of rapid deployment or disposition on a patient suffering from, e.g., a heart attack or other incident requiring immediate cardiac support.

SUMMARY OF THE INVENTION

The present invention is a portable device and the method for the application of emergency CPR in remote locations, comprising the use of a thoracic garment having fastening means, at least one bladder, inflation or flexure means for the bladder, and control means for the inflation or flexure means. Means for controlling or monitoring, or both, the cardiac and/or pulmonary functions of a victim can be further provided, as can auxiliary power to operate the device during or until transfer of the victim to a primary-care facility.

DESCRIPTION OF THE PREFERRED EMBODIMENTS

The present invention comprises the use of portable apparatus, and the apparatus itself, or a unit which can be stored in a wide variety of locations, and which can therefore provide emergency field CPR support for a person whose vital functions require assistance; it comprises a vest-like thoracic garment which can be quickly fastened about the chest area of the victim, and having at least one flexible bladder or flexure means which can rapidly be brought to bear in a position to begin artificial CPR. Anterior and posterior contacts permit defibrillation if necessary, without removal of the vest. Various control and energy-storage devices provide energy to drive energy-using systems integral with the thoracic garment, such as inflation-control valves and the defibrillation paddles, and control circuitry. The control circuitry is operatively interconnected with the devices for providing heart or lung stimulation, assistance or control, including parts of the apparatus necessary to provide energy to the devices. Standby and parallel circuits can be included to provide auxiliary power to maintain the operation of the vest beyond normal battery life, or to continue functions while the victim is being transferred to a primary-care facility. The invention permits rapid attention to, e.g., a heart-attack victim virtually within seconds of the occurrence, thereby increasing the chances of survival for the victim.

The term "operatively interconnected", as used in this specification, refers to the interaction among sensor means employed in the apparatus of this invention, wherein the sensor means provides a signal to a control circuit, e.g., an IC, and either responsive or initial programming of the control circuit then causes it to route energy to an activating means such as, e.g., a valve, solenoid, firing circuit or the like; in some cases the control circuit can serve multiple functions, such as, e.g., causing the operation of a valve or solenoid and simultaneously or sequentially activating an event timer, sequence counter, display means or the like.

The preferred embodiment of the present invention is a portable device for the prompt application of CPR in remote locations, comprising a thoracic garment or vest having fastening means, at least one bladder or flexure means integral with the vest, control and inflation means for the bladder or operating and control means for the flexure means. The bladders and flexure means are so located that when the vest is placed on the victim of a cardiac or pulmonary ocurrence, the bladders or flexure means are so located that they are in correct position to be effective for a substantial number of normal adults.

Means for controlling and monitoring the cardiac and/or pulmonary functions of a victim can be further provided, as can auxiliary power to operate the device during or until transfer of the victim to a primary-care facility.

Figure 1:
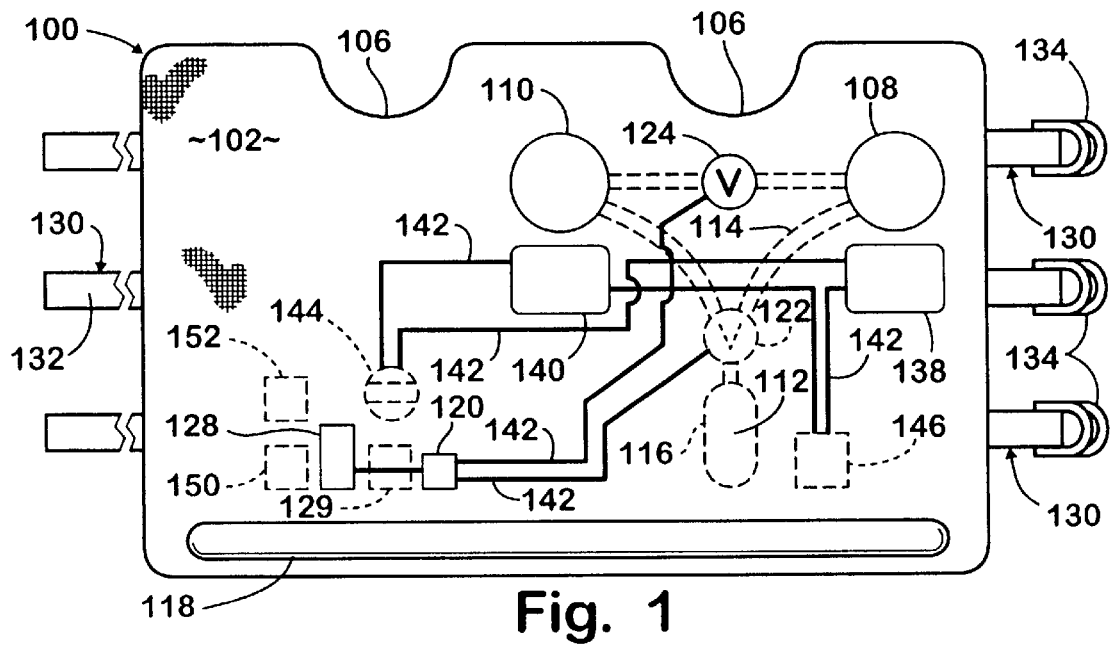
FIG. 1 is a view in perspective of the inner surface of the vest of this invention.
Figure 2:
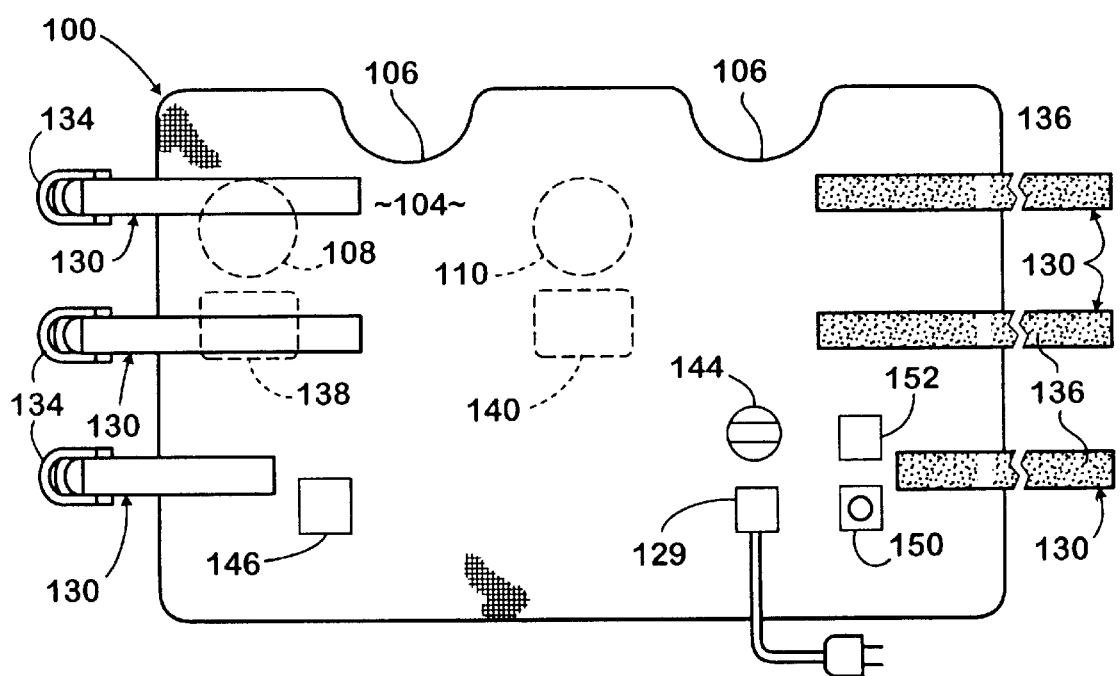
FIG. 2 shows the outer surface.

Referring now to FIGS. 1 and 2, vest 100 has an inner surface 102 and outer surface 104. Vest 100 is conveniently provided with relieved portions 106 which fit under a victim's arms whereby the main upper portion of the vest bears on the victim's upper torso, and especially in the thoracic region. At least one flexure means or bladder 108 is provided in the inner surface 102 of vest 100, juxtaposed in such fashion that when vest 100 is fastened about the upper torso of an adult, bladder 108 bears substantially on the cardiac region of the chest. For the best operation of vest 100, bladder 108 is a first bladder; a second bladder 110 is provided in inner surface 102, complementary in position to first bladder 108, such that substantially simultaneous inflation of the two bladders results in a compression of the chest of the victim in the region of the heart, thereby causing at least a partial heart beat. Bladders 108 and 110 are so integrated into vest 100 that they are efficient in providing cardiac assistance or stimulation for a substantial portion of the adult population. Repetitive compression and exhaustion of the bladders provides a rhythmic heart and circulatory function. Vest 100 preferably further has means for providing pulmonary assistance, as discussed further hereinbelow. Means 118 provides restraint for the abdominal region in order to prevent the abdomen from distending during pulmonary or cardiac assitance, and can be any convenient means such as, e.g., a belt, a strap, or a bladder operatively separate from bladders 108 and 110, and having its own inflation means, wherein that inflation means exerts only sufficient pressure to prevent abdominal distension, hut not enough to cause abdominal distress.

Either or both bladders 108 or 110 are conveniently filled with a compressible fluid, e.g., air or other gas 112 under pressure, the gas passing through channels shown here as flexible inflating tubes 114. In one embodiment, the gas is pure oxygen or an oxygen-enriched mixture suitable for assisting breathing. The source of gas 112 is container 116 or other means discussed more fully hereinbelow. In order to provide a pulsating function, bladders 108 and 110 are necessarily filled and exhausted in a fashion which will cause a substantially simulated heart action; integrated-circuit (IC) means 120 provides signals to cause inflating valves 122 and deflating valves 124 to open and close sequentially and thus serve as a flexure means for the bladders. The output parameters of IC 120 can be changed as necessary or desirable by manipulation of circuit control 152 during operation of the garment 100 as the response of the victim dictates. Circuit means 120 is well known to those skilled in the art, and apart from the present invention, is not claimed as inventive per se. Bladders 108 and 110 are thus inflated with gas 112 from container 116 throuugh inflating tubes 114 connected between the bladders and container 116 through inflating valve 122, and deflated upon activation of deflating valve 124 through tube 126 connected to the bladders and permitting exhaustion to the ambient atmosphere. Power for IC means 120 and valves 122 and 124 is conveniently provided by battery or other suitable energy source 128 including, e.g., conventional 125- or 250-volt 60-Herz current. IC means 120 is preferably programmed with a default value to cause bladders 108 and 110 to function at an optimal rate. The circuit can also he programmed to be capable of changing any parameter such that, e.g., the default heart-stimulation rate can be increased or decreased during the operation of the apparatus of the invention.

Fastening means 130 can be any convenient means known to those skilled in the art, and is shown in FIG. 1 as at least one strap 132 affixed to one portion of outside surface 104, and receiving or ring portion 134 affixed to a complementary site on outer surface 104, whereby vest 100 may he securely and adjustably fastened about the torso of a victim of a heart attack or other medical circumstance. To provide a wide range of adjustment, straps 132 are conveniently provided with hook-and-loop-pile fabric, sometimes known as velcro, along a substantial portion of their length.

In one embodiment of the device of the present invention, anterior contact means 138 and posterior contact means 140 are integral with the thoracic garment, and positioned in inner surface 102 for either or both cardiac-function monitoring and defibrillation. Contact means 138 and 140 are fastened or integrated in such manner as to be properly positioned for the majority of the adult population when vest 100 is placed about the torso of an adult victim and fastened with means 130. Conduction means, shown in FIG. 1 as wires 142, carry condition-monitoring signals from contact means 138 and 140 to display means 144, or energy from defibrillator control means 146 to contact means 138 and 140. Plug means or contact 148 is provided for the connection of external power if needed for defibrillator-control means 146. Master switch 150 interfaces power source 128 with the various operating and instrumental moieties of this invention which require energy for their function. Control means 146 comprises at least one integrated circuit programmed to receive information from contact means 138 and 140, and in response to those signals, to send power to contact means 138 and 140, whereby defibrillation operates in response to the victim's condition. Control means 146 can he programmed with a default value to cause the operating moiety to function at an optimal rate. The circuit can also be programmed to be capable of changing parameter such that, e.g., the default defibrillation rate can he increased or decreased during the operation of the apparatus of the invention.

In the method of the operation of the vest of the present invention, a person in the proximity of the victim positions the open vest about the upper torso of the victim, closes and fastens the vest properly and securely with fastening means 130, and activate master switch 150, generally in less than a minute of elapsed time, and in almost any event, in sufficient time to diminish significantly the likelihood of irreversible physiological damage. Activation of master switch 150 then causes energy from source 128 to flow into circuit 120; circuit 120 thereupon directs sequential inflation and deflation of bladders 108 and 110, or other means to cause heart and/or pulmonary stimulation, as described herein. Mask 402, shown in FIG. 7, can be emplaced promptly after the garment has been fastened and switch 150 activated.

Figure 3:
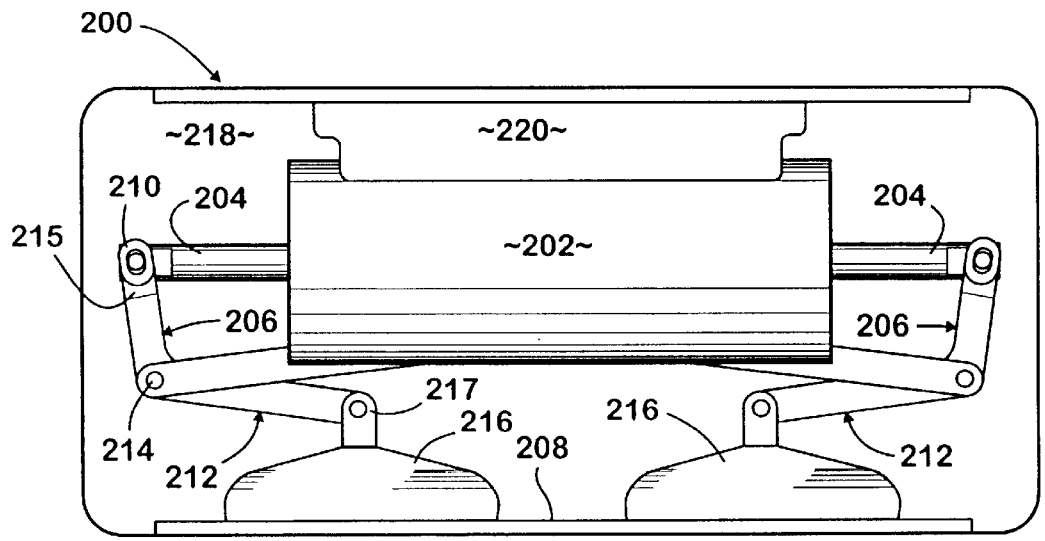
FIG. 3 is a cutaway view of the compression assembly of the invention.

An alternative means for providing pressure in the thoracic region of a heart-attack victim is shown as flexure means or compression assembly 200 in FIG. 3, in where energization of solenoid or equivalent activation means 202, controlled by IC means 120, provides signals to cause operation of lever-activation means 204, whereby lever system 206 causes a rapid extension of one surface 208 of compression assembly 200; In a fashion similar to the control of the inflation and deflation of bladders 108 and 110, the output parameters of IC 120 can be changed as necessary or desirable by manipulation of circuit control 152 during operation of the garment 100 as the response of the victim dictates. Surface 208 is composed at least partly of flexible material, preferably a dilatantic elastomer chosen from the group consisting of silicone and un-crosslinked polybutadiene. Other elastomers are also within the scope and spirit of this invention. Compression assembly 200 is integral with thoracic garment 100 and is placed, and surface 208 is necessarily juxtaposed, in inner surface 102, within vest 100, in such fashion that when vest 100 is fastened about the upper torso of the victim, flexible surface 208 bears upon the proper portion of the victim's torso.

Flexure means or lever system 206 comprises elongated pivot means 210 whereby lever 212 is connected mechanically with lever-activation means 204; lever 212, having upper end 215 and foot end 217, moves about pivot 214, and causes foot 216 attached to foot end 217 to bear on flexible surface 208, causing the exterior of that surface to bear in turn upon the upper torso of the victim. The portion 218 of compression assembly 200 on the side away from flexible surface 208 is a rigid or semi-rigid material, and is formed of metal such as, e.g., titanium, stainless steel, or the like, of engineering plastic such as, e.g., polycarbonate, polyamide, polyimide, or acrylonitrile-butadiene-styrene, or a composite comprising a fiber-reinforced plastic material. Those skilled in the art will realize that ail substances used forming the vest and its constituent moieties are preferably chosen from those materials unlikely to interact inimically with the human body.

Solenoid 202 is rigidly affixed to semi-rigid portion 218 by assembly 220, whereby the thrust generated by the action of lever system 206 is transmitted to portion 218. Energy is supplied to solenoid 202 through wires 142 from energy source 128 in response to signals from control circuit 128, which is programmed to provide rate control. Those skilled in the art will realize that vest 100 preferably comprises a plurality of compression assemblies 200, arranged to provide substantially simultaneous anterior and posterior pressure.

Figures 4, 5:
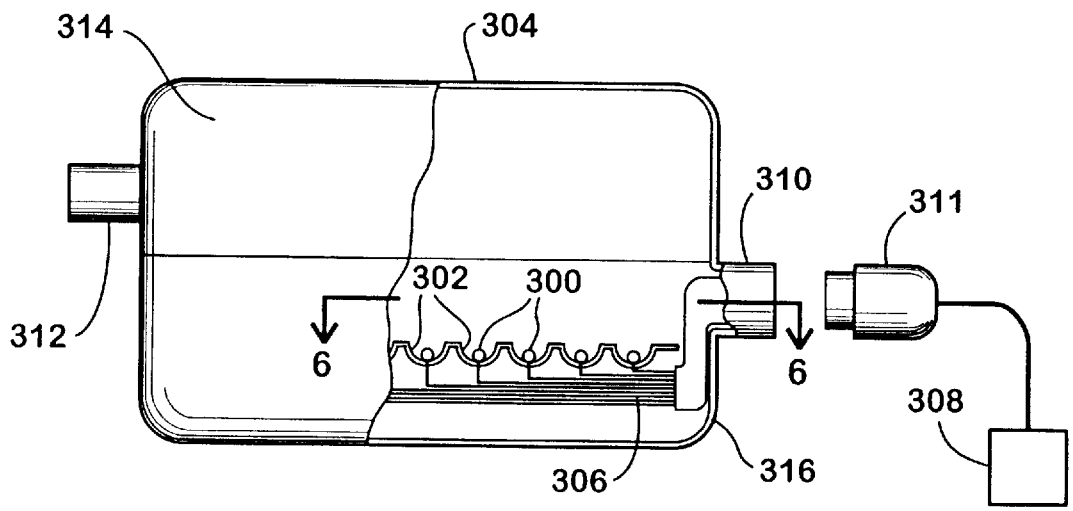
FIG. 4 is a partially cut-away elevation of the gas-generating container of the invention.
FIG. 5 schematically represents the control circuit for the gas-generating means.
Figure 6:
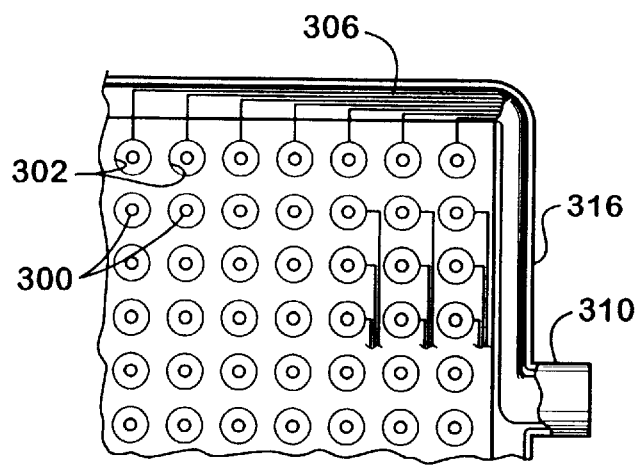
FIG. 6 is a section taken along lines 6—6 of FIG. 4.

Another embodiment of the means for inflating bladders 108 and 110 is shown in FIGS. 4, 5 and 6. Gas-generation materials 300 such as, e.g., sodium azide ($NaN_3$), one or more reactive-chemical material mixtures, and the like, are disposed in suitable form such as, e.g., pellets, in at least one individual, and preferably a plurality of, contained in segments 302 in container 304. Operating circuit 306 is disposed within container 304, and serves to provide energy to initiate the decomposition of the gas-generating pellets 300. Circuit 306 is preferably a printed circuit for most reliable implementation of the timing and sequence of the gas-generation steps. IC 308 shown in FIG. 5, serves as control of the timing of the initiation of the decomposition of pellets 300 and the sequential operation of valves 122 and 124. As in the case of inflation of bladders 108 and 110 from container 116, inflating tubes 114 and deflating tubes 126 convey gas from container 304 and then to the ambient atmosphere in order to deflate the respective bladders.

Container 304 is necessarily gas-tight, and preferably comprises a plurality of separable portions to permit loading of pellets 300 into segments 302. Refering to FIGS. 5 and 6, container 304 further comprises female connection means 310 to provide for input from IC 308 through male connection means 311 to circuit 306. Connection port 312 provides gas communication with inflating tubes 114. The respective compositions and sizes of pellets 300, and sizes of container 304, and bladders 108 and 110 are interrelated, and subject to calculation to produce the desired pressure within the bladders. It is within the scope and spirit of this invention that pellets 300 can be chosen of a composition and size sufficient to generate more pressure than required to inflate bladders 108 and 110 only a single tine, and that pressure thus generated can be regulated by the operation of valves 122 and 124 as heretofore described.

Container 304 conveniently comprises an assembly of portions, shown in FIG. 4 as upper portion 314 and lower portion 316. Lower portion 316 has segments 302 disposed therein, wherein pellets 300 are placed; there is in each segment 302 a terminal, or contact, of circuit 306, whereby each pellet 300 may be energized, or fired, in appropriate sequence upon command from IC 308, thus to generate pressure within the system.

In the operation of the present invention wherein bladders 108 and 110 are inflated by gas generated within container 304, activation of master switch 150 causes an electrical signal to flow to IC 308. IC 308 has a clock, or event-timer, function as part of its internal circuitry, and is programmed to send sequential trigger, or firing, signals through operating circuit 306 to segments 302 such that individual pellets 300 are caused to decompose, whereby gas flows from container 304 through tubes 114 and valves 122 into bladders 108 and 110, to cause inflation of the bladders and concomitant thoracic pressure. Valves 124 then permit deflation of the bladders through tubees 126, and following the closing of valves 124, the cycle can be repeated. The timing of the inflation/deflation cycle, and thus of the cardiac-stimulation rate, is a programmable function of IC 308; that function is set at a default rate based upon medical knowledge, but can be changed as necessary or desirable by manipulation of circuit control 152 during operation of the garment 100 as the response of the victim dictates. In one embodiment, the regulation of the rate of bladder inflation can be achieved by the rate of gas generation by decomposition of pellets 300, and valves 122 are unnecessary. In this embodiment, valves 124 are still used for deflation.

In one embodiment of the invention, a device for pulmonary assistance is supplied, whereby the victim of a situation affecting heart action can be provided with an oxygen-enriched gaseous medium for assistance in breathing; such a device is preferably a mask which fits over the victim's mouth and nose, but can he any breathing-assistance means other than the ambient atmosphere, whereby oxygen is conveyed to the victim. The breathing-assistance means can include a tube serving both to prevent the victim's tongue from blocking the throat, and to convey oxygen to the victim's breathing passage.

Figure 7:
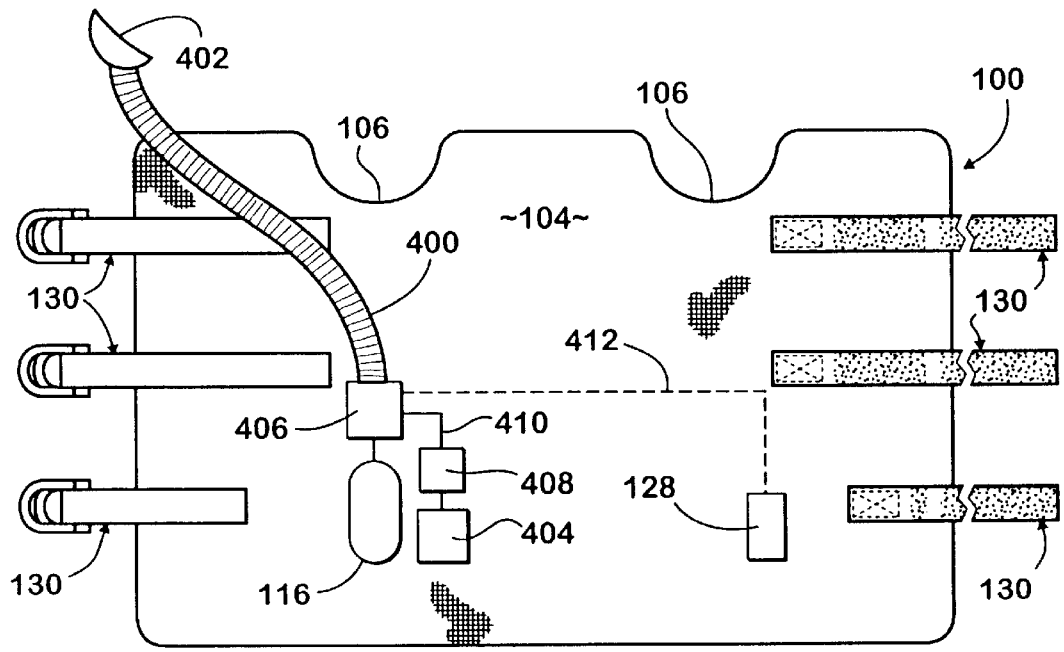
FIG. 7 shows an embodiment with auxiliary breathing apparatus incorporated.

FIG. 7 shows vest 100 with integral pulmonary-assistance means. Whereby gas container 116 has flexible tube 400 connected thereto at one end; the other end of flexible tube 400 is affixed to breathing mask 402, the connections at both ends being substantially gas-tight, whereby a breathing mixture, preferably oxygen-enriched, can he conveyed to a victim of either or both a cardiac or pulmonary problem. Gas 112 flows through tube 400 upon operation of valve 406; the operation of valve 406 is controlled by IC 408. IC 408 causes valve 406 to operate independently of, but in cooperation with, either inflating and deflating valves 122 and 124, compression assembly 200, or bladder operation as controlled by IC 308 in such fashion that heart stimulation is maintained at a rate different from, but related to, that of pulmonary assistance; that is, the thoracic region may be compressed and relaxed, e.g., from about 60 to about 70 times per minute, while valve 406 operates to provide air or oxygen from about 15 to about 20 times per minute. The output parameters of IC 408 can be changed as necessary or desirable by manipulation of circuit control 404 during operation of the garment 100 as the response of the victim dictates.

Wires 410 convey operating signals from IC 408 to valve 406; wires 412 provide operating current from energy source 128 to valve 406. Valve 406 can be any of a number of types well known to those skilled in the art, and the precise mode of its operation, other than as a gas-regulation means, is not part of this invention per se.

Modifications and improvements to the preferred forms of the invention disclosed and described herein may occur to those skilled in the art who come to understand the principles and precepts hereof. Accordingly, the scope of the patent to he issued hereon should not be limited solely to the embodiments of the invention set forth herein, but rather should be limited only by the advance by which the invention has promoted the art.

What is claimed is:

1. A portable apparatus to provide emergency field cardiopulmonary resuscitation support for a person whose vital functions require assistance, comprising:

a thoracic garment having an inner surface, an outer surface, fastening means, a plurality of bladders, and valves operatively interconnected therewith for control of inflation and deflation of the bladders, the thoracic garment further having integral therewith, anterior contact means and posterior contact means;

at least one inflatable bladder integral with the thoracic garment;

inflation means for the bladder;

control means operatively interconnected with the inflation means; and a compression assembly including a semi-rigid surface and a flexible surface, and including a lever system having a connection means whereby at least one lever having an upper end and a foot end is connected mechanically with lever-activation means such that the lever moves about a pivot to cause the upper end to bear upon the semi-rigid surface, and to cause the foot end to bear upon the flexible surface, wherein the exterior of the flexible surface bears upon the upper torso of the person.

2. The apparatus of claim 1 wherein the flexible surface is composed at least partly of flexible elastomer.

3. The apparatus of claim 1 wherein the flexible surface is composed at least partly of flexible dilatantic elastomer chosen from the group consisting of silicone and un-crosslinked polybutadiene.

4. A portable apparatus to provide emergency field cardiopulmonary resuscitation support for a person whose vital functions require assistance, comprising:

a thoracic garment having an inner surface and an outer surface and fastening means;

at least one inflatable bladder integral with the thoracic garment;

inflation means for the bladder, the inflation means including at least one gas-tight container having disposed therein at least one gas-generating material, wherein the gas-tight container is operatively interconnected by gas-tight means to the bladder through tubing and an inflating valve, and the bladder is exhausted to atmosphere through tubing and an exhaust valve, the gas-tight container comprising a plurality of separable portions; and control means operatively interconnected with the inflation means.

5. A portable apparatus to provide emergency field cardiopulmonary resuscitation support for a person whose vital functions require assistance, comprising:

a thoracic garment having an inner surface and an outer surface and fastening means;

at least one inflatable bladder integral with the thoracic garment;

inflation means for the bladder, the inflation means including at least one gas-tight container having disposed therein at least one gas-generating material, wherein the gas-tight container is operatively interconnected by gas-tight means to the bladder through tubing and an inflating valve, and the bladder is exhausted to atmosphere through tubing and an exhaust valve, the gas-tight container including individual segments and a reactive chemical material in pellet form disposed in the individual segments and including a circuit disposed within the container, wherein the circuit is operatively interconnected with an energy source and serves to provide energy to initiate decomposition of the gas-generating pellets, whereby a gas is generated to inflate the bladders; and control means operatively interconnected with the inflation means.

6. A method of providing emergency field cardiopulmonary resuscitation which comprises:

providing and positioning about the upper torso of a person whose vital functions require assistance, an open thoracic garment having an inner surface, an outer surface, and fastening means;

providing a plurality of inflatable bladders integral with the thoracic garment;

providing inflation means for the bladders, the inflation means including a gas generated within a container upon activation of a master switch, the switch causing an electrical signal to flow to an integrated circuit, the integrated circuit thereupon sending firing signals through an operating circuit to pellets in pellet-containing segments disposed in a gas-tight container having circuit means such that individual pellets are caused to decompose to produce a gas, whereby gas flows from the contain through tubes into the bladders, whereby the bladders are inflated;

providing a master switch and control means operatively interconnected with the inflation means;

the step of closing and fastening the garment; and the step of activating the master switch.

7. The method of claim 6 wherein deflating valves permit deflation of the bladders after the inflation step.

8. The method of claim 6 wherein the container is gas-tight.

9. The method of claim 7 wherein the container has a plurality of separable potions.

\* \* \* \* \*